(12) United States Patent
Lenna et al.

(10) Patent No.: US 9,650,410 B2
(45) Date of Patent: *May 16, 2017

(54) PROCESS FOR THE PREPARATION OF ABIRATERONE AND ABIRATERONE ACETATE

(71) Applicant: INDUSTRIALE CHIMICA S.R.L., Milan (IT)

(72) Inventors: Roberto Lenna, San Giorgio su Legnano (IT); Riccardo Di Brisco, Trecate (IT)

(73) Assignee: INDUSTRIALE CHIMICA S.R.L., Milan (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/908,816

(22) PCT Filed: Jul. 29, 2013

(86) PCT No.: PCT/IB2013/056206
§ 371 (c)(1),
(2) Date: Jan. 29, 2016

(87) PCT Pub. No.: WO2015/015246
PCT Pub. Date: Feb. 5, 2015

(65) Prior Publication Data
US 2016/0168192 A1 Jun. 16, 2016

(51) Int. Cl.
C07J 1/00 (2006.01)
C07J 43/00 (2006.01)
C07J 31/00 (2006.01)

(52) U.S. Cl.
CPC ........... C07J 43/003 (2013.01); C07J 31/006 (2013.01)

(58) Field of Classification Search
CPC ............................. C07J 1/0011; C07J 43/003
USPC ............................................ 540/95; 552/640
See application file for complete search history.

(56) References Cited

FOREIGN PATENT DOCUMENTS

WO 93/20097 A1 10/1993
WO 2006/021777 A1 3/2006

OTHER PUBLICATIONS

Potter, et al., Organic Preparations and Procedures, 29(1): 123-134 (1997).
International Search Report for PCT/IB2013/056206 dated Mar. 17, 2014 (3 pages).
Sun, Q., et al., "Pd(PPh3)4/AgOAc-catalyzed coupling of 17-steroidal triflates and alkynes: Highly efficient synthesis of D-ring unsaturated 17-alkynylsteroids," Steroids, Elsevier Science Publishers, New York, NY, US, vol. 75, No. 12, pp. 936-943 (Dec. 1, 2010).
Navendu, Jana, et al., "Development of a Suzuki Cross-Coupling Reaction between 2-Azidoarylboronic Pinacolate Esters and Vinyl Triflates to Enable the Synthesis of [2,3]-Fused Indole Heterocycles," The Journal O Forganic Chemistry, vol. 79, No. 6, pp. 2781-2791 (Mar. 21, 2014).

*Primary Examiner* — Brenda Coleman
(74) *Attorney, Agent, or Firm* — Abelman, Frayne & Schwab

(57) ABSTRACT

The present invention relates to a novel process for the synthesis of abiraterone, and in particular of abiraterone acetate, compound of formula (I) reported below: N O (I) which has pharmacological activity useful for slowing down the progression of prostate cancer at an advanced stage. The process is characterized by an intermediate step wherein DHEA-acetate is triflated using Ar—N(OTf)$_2$ as the triflation reagent.

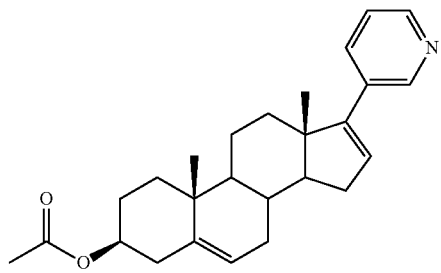

10 Claims, No Drawings

PROCESS FOR THE PREPARATION OF ABIRATERONE AND ABIRATERONE ACETATE

RELATED APPLICATIONS

This application is a rational phase of Application No. PCT/IB2013/056206 filed Jul. 29, 2013, incorporated by reference in its entirety.

FIELD OF THE INVENTION

The present invention relates to the field of processes for the synthesis of active ingredients for pharmaceutical use and in particular to a process for the preparation of abiraterone and abiraterone acetate on an industrial scale.

BACKGROUND OF THE INVENTION

The compound of formula (I) reported below, the chemical name of which is (β)-17-(pyridin-3-yl)androsta-5,16-dien-3-ol acetate, is commonly referred to by the name abiraterone acetate:

Abiraterone acetate is a steroid with pharmacological activity that is useful for slowing down the progression of prostate cancer at an advanced stage.

Carcinoma of the prostate is the principal tumor in the male population in Western countries, where it is also the second cause of cancer death.

Abiraterone acetate has proved capable of prolonging the life of these patients and of improving their quality of life, and is the first element of a new class of non-chemotherapeutic medicinal products with targeted action, that are capable of acting directly on the self-feeding process of the tumor.

Advanced prostate carcinoma cells are able to autonomously synthesise testosterone from cholesterol, single-handedly feeding its own growth and development thanks to the CYP17 enzyme, which is a key element of the synthesis of androgens and, in particular, of testosterone.

Abiraterone acetate is an efficient inhibitor of the CYP17 enzyme and is thus a medicinal product that is able to deeply inhibit the production of testosterone and other androgen hormones by acting at the level of the adrenal gland, the testis and, above all, of the tumor microenvironment.

Abiraterone acetate is described for the first time in international patent application WO 93/20097 A1. Example 1 of this application describes the preparation of abiraterone acetate (I) from prasterone acetate (III) according to the following scheme:

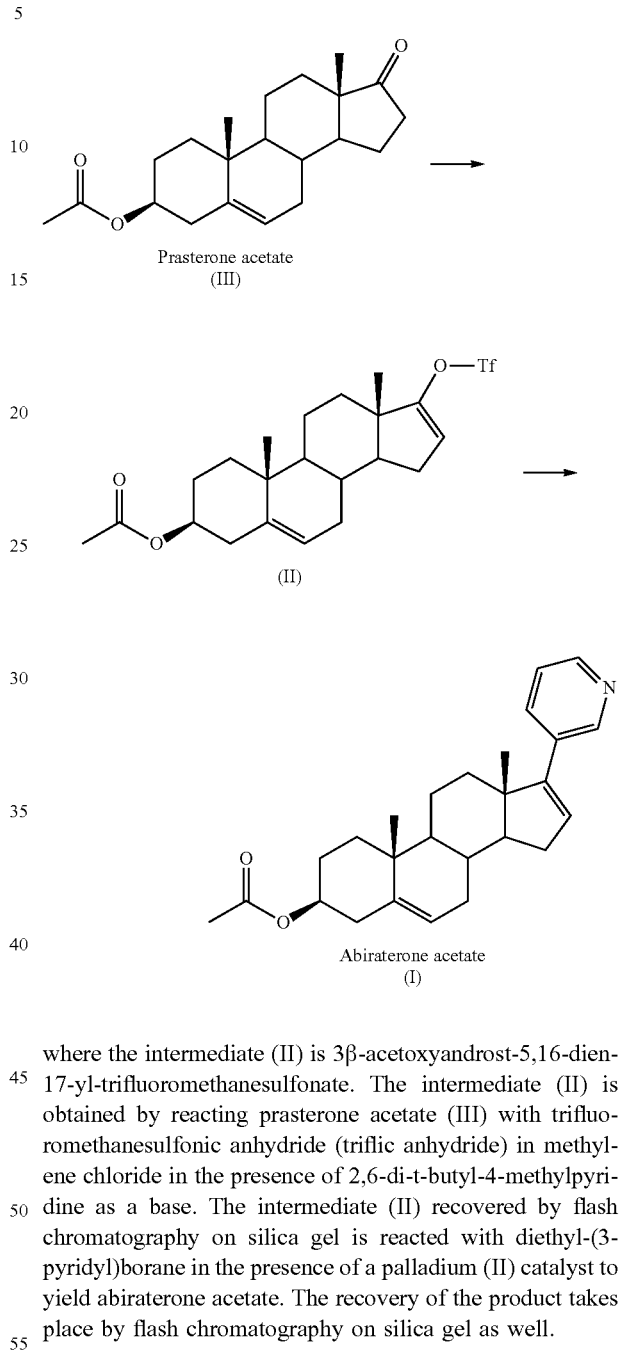

where the intermediate (II) is 3β-acetoxyandrost-5,16-dien-17-yl-trifluoromethanesulfonate. The intermediate (II) is obtained by reacting prasterone acetate (III) with trifluoromethanesulfonic anhydride (triflic anhydride) in methylene chloride in the presence of 2,6-di-t-butyl-4-methylpyridine as a base. The intermediate (II) recovered by flash chromatography on silica gel is reacted with diethyl-(3-pyridyl)borane in the presence of a palladium (II) catalyst to yield abiraterone acetate. The recovery of the product takes place by flash chromatography on silica gel as well.

An alternative synthesis is described in *Organic Preparations and Procedures Int.*, 29 (1), 123-134 (1997). According to the authors this new preparation would overcome the problem of a large-scale production of abiraterone, not resolved by the afore-described syntheses. The synthesis scheme (set out below), actually, seems of doubtful industrial applicability, not so much on account of the fact that there are four reactions involved compared to the two reactions of the synthesis of WO 93/20097 A1, but because the reagent necessary for obtaining the "hydrazone" intermediate is hydrazine, a known carcinogenic product.

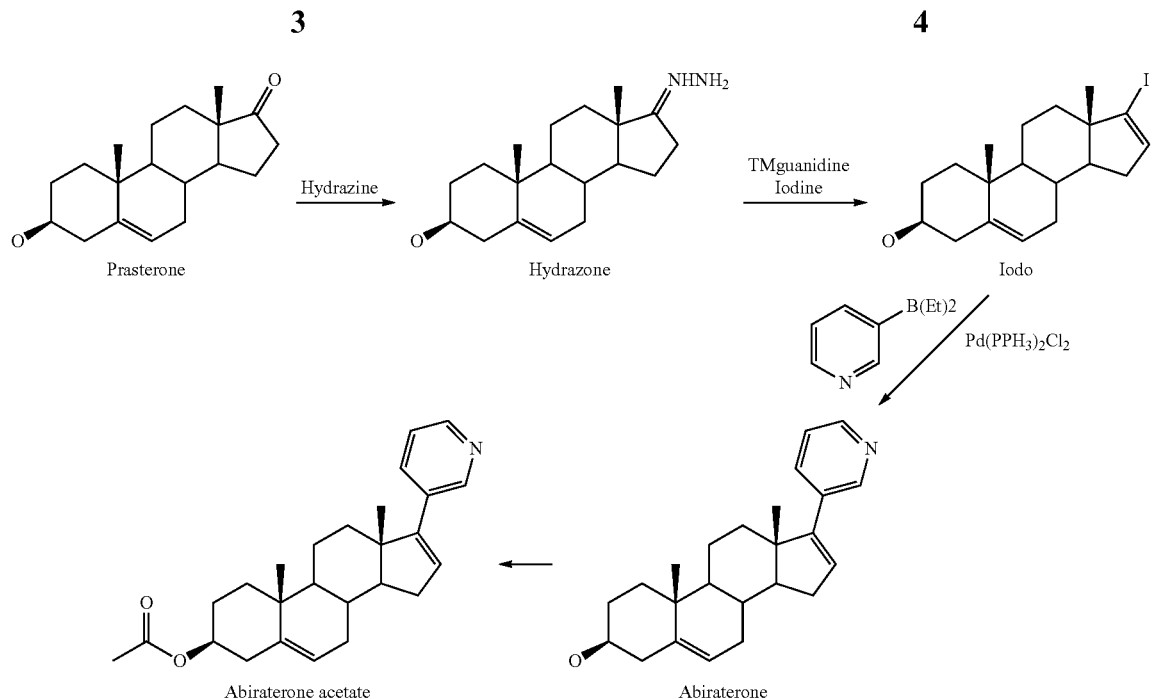

International patent application WO 2006/021777 A1 describes and claims an optimisation of the process of WO 93/20097 A1, based on the study of the reaction conditions. According to the inventors (WO 2006/021777 A1, p. 3), the described process keeps within acceptable levels the formation of the impurity of formula:

and eliminates the need for chromatographic purifications.

The key element of this new process is the choice of base to be employed in the reaction from prasterone acetate (III) to intermediate (II), which is selected from the tertiary or heterocyclic amines pyridine, 2,6-lutidine, N-methylmorpholine, trimethylamine, triethylamine, 1,4-diazabicyclo[2.2.2]octane (DABCO), N,N-diisopropylethylamine (DIPEA), 1,8-diazabicycloundec-7-ene (DBU) and 1-azabicyclo[2.2.2]octane (commonly known as quinuclidine). The formation of the intermediate (II) is obtained in this process with a yield of 60% (example "Triflate formation 3", p. 14 of WO 2006/021777 A1); the reported yield is in fact 80% of a 3:1 mixture of intermediate (II) and starting prasterone acetate. The example "Salt formation" on p. 15 describes the formation of the methanesulfonate of abiraterone as a purification method of the latter from the unreacted portion of prasterone. In this case too, the proposed synthesis route does not appear to be of real industrial applicability: as can be read from the example, the obtained salt is crystallised from isopropanol, but in these conditions a methanesulfonic acid ester is formed, and it is known that these esters are genotoxic and must therefore be eliminated from the final product.

There remains thus a need in the field for a synthesis process of abiraterone or abiraterone acetate of real applicability on an industrial scale.

SUMMARY OF THE INVENTION

The present invention relates to a novel process for the production of abiraterone acetate according to the scheme:

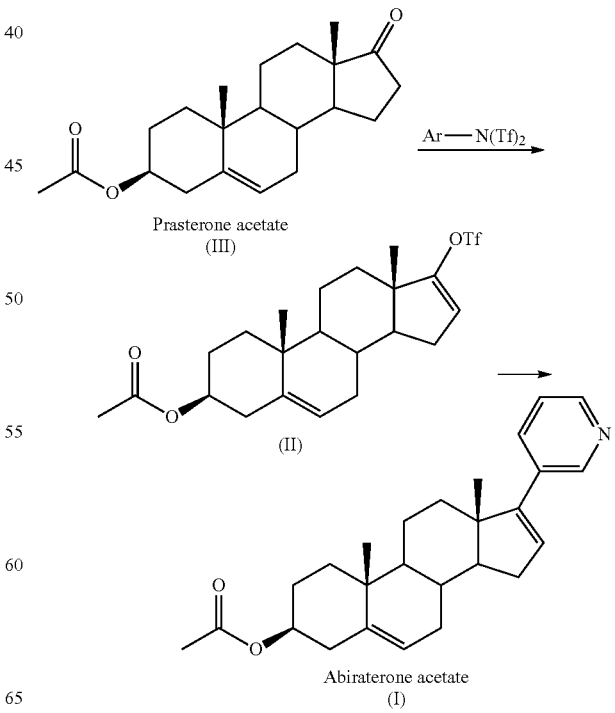

characterised by the reaction of prasterone acetate (III) with an aromatic bis(trifluoromethanesulfonimide) of general formula Ar—N(Tf)$_2$, wherein Ar is the aromatic radical and the N(Tf)$_2$ group is the radical:

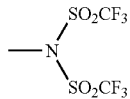

In this reaction, the intermediate (II) 3β-acetoxyandrost-5,16-dien-17-yl-trifluoromethanesulfonate is formed, which can then be transformed into abiraterone acetate.

The reaction object of the invention is also applicable to the synthesis of abiraterone by simply employing prasterone as starting reagent instead of prasterone acetate.

The synthesis process of the present invention prevents the formation of the impurity

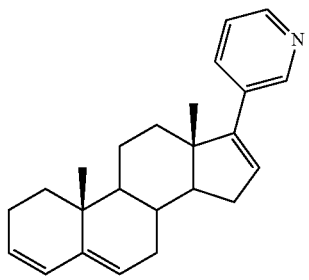 [SMILES: C[C@]12CCC=CC1=CCC1C2CC[C@]2(C)C(c3cccnc3)=CCC12]

the quantity of which could only be limited in the process of WO 2006/021777 A1.

DETAILED DESCRIPTION OF THE INVENTION

The present invention relates to a novel process for the production of Abiraterone acetate in which fundamental is the reaction of prasterone acetate (III) with an aromatic bis(trifluoromethanesulfonimide) of general formula Ar—N(Tf)$_2$ and a basis for obtaining the intermediate of formula (II), which is then further reacted to abiraterone acetate; the bis(trifluoromethanesulfonimide) is commonly known in the field by the abbreviations tiflimide or Tf.

The aromatic radical of tiflimide Ar—N(Tf)$_2$ can be of any type, mono- or polycyclic, of hydrocarbon type (for example, a phenyl or naphthalene radical), heterocyclic, or of mixed type, formed by a heterocyclic ring fused with a hydrocarbon ring, which in this latter case can also be saturated; the Ar radical can also be substituted. The preferred tiflimides for the purposes of the invention are those corresponding to the general formulae (IV) or (V) set out below

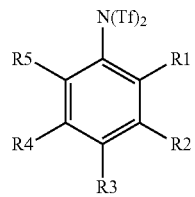

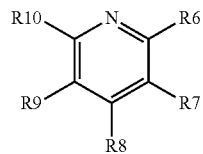

wherein:
the aromatic radical is derived from phenyl or pyridine;
R1, R2, R3, R4 and R5, independently of each other, can be hydrogen, halogen, —NO$_2$, a linear or branched alkyl radical, an RCONH— amide radical or an RO— alkoxide radical, wherein R is a linear or branched alkyl group; and
one of R6, R7, R8, R9 and R10 is the —N(Tf)$_2$ radical, while the remaining radicals between R6 and R10, independently of each other, have the same meanings as reported above for radicals R1-R5.

Preferably, Ar—N(Tf)$_2$ is N-phenyl-bis(trifluoromethanesulfonimide) or N-(2-pyridyl)-bis(trifluoromethanesulfonimide).

The amount of tiflimide is between 0.8 and 2 times by weight with respect to the starting prasterone acetate.

The reaction solvent is selected from toluene, xylene, diethyl ether, methyl tertbutyl ether, tetrahydrofuran (THF), methyltetrahydrofuran, chloroform, dichloromethane and 1,2-dichloroethane. Preferred solvents are ethers, for example tetrahydrofuran.

The employable base is selected from potassium hexamethyldisilazane $(((CH_3)_3Si)_2NK$, known by the abbreviation KHMDS), lithium hexamethyldisilazane $(((CH_3)_3Si)_2NLi$, abbreviated LiHMDS), sodium hexamethyldisilazane $(((CH_3)_3Si)_2NNa$, abbreviated NaHMDS); lithium diisopropylamide (LDA), lithium tri-sec-butylborohydride (known as L-selectride), potassium tri-sec-butylborohydride (K-selectride) and sodium or potassium tert-butoxides.

The reaction temperature is between −80° C. and 30° C., while the reaction time is between 2 and 24 hours.

Once the intermediate of formula (II) has been obtained, it can be transformed into abiraterone acetate (I) by reacting the mixture resulting from the first step as described above with diethyl borane in the presence of a palladium (II) catalyst such as, for example, bis(triphenylphosphine)palladium(II)dichloride, Pd(PPh$_3$)$_2$Cl$_2$. The abiraterone acetate thus formed is separated from the reaction mixture by salification with an acid; the abiraterone acetate is then recovered by treatment with an aqueous base, and the resulting product is purified by known methods such as crystallisation from solvent or silica gel chromatography.

The process of the invention is also applicable to the synthesis of abiraterone simply using prasterone as starting reagent instead of prasterone acetate.

The invention will be further illustrated by the following examples, which are provided by way of an illustrative and non-limiting example of the present invention. The reagents used in the examples are commonly available commercially and are used without the need for further purifications.

Example 1

This example relates to the characterising step of the invention, i.e. the preparation of the intermediate (II) 3β-acetoxyandrost-5,16-dien-17-yl-trifluoromethanesulfonate from prasterone acetate (III).

A solution of prasterone acetate (1 g) and N-phenyl-bis (trifluoromethanesulfonimide) (1.3 g) in tetrahydrofuran (15 ml) is cooled to −78° C. under agitation.

6.05 ml of a 0.5 molar solution of potassium hexamethyldisilazane in toluene are slowly added and agitation is maintained for 2 hours at a temperature between −80 and −70° C. The temperature of the reaction mixture is then brought to 0÷5° C. and maintained for a further 2 hours.

16 ml of isopropyl acetate and 16 ml of saturated aqueous solution of ammonium chloride are added. The phases are separated and the organic phase is washed with 32 ml of 1M aqueous HCl solution and with 32 ml of saturated aqueous solution of NaCl.

The solvent is removed under reduced pressure thus obtaining a colourless oil, which titrated by HPLC analysis against authentic samples proves to principally comprise prasterone acetate (214 mg) and intermediate (II) 970 mg.

The colourless oil is crystallised from ethanol thus obtaining, after drying at 45° C. and reduced P, 850 mg of intermediate (II).

Example 2

This example illustrates a complete preparation of abiraterone acetate (I) starting from prasterone acetate (III).

A solution obtained by dissolving 6.15 g of prasterone acetate and 8 g of N-(2-pyridyl)-bis(trifluoromethanesulfonimide) in 92.5 ml of tetrahydrofuran is cooled to −78° C. under agitation.

37.3 ml of a 0.5 molar solution of potassium hexamethyldisilazane in toluene are slowly added and agitation is maintained for 2 hours at a temperature between −80 and −70° C. The temperature of the reaction mixture is then brought to 0÷5° C. and maintained for a further 2 hours.

100 ml of isopropyl acetate and 100 ml of saturated aqueous solution of ammonium chloride are added. The phases are separated and the organic phase is washed with 100 ml of 1M aqueous HCl solution and with 100 ml of saturated aqueous solution of NaCl.

The solvent is eliminated under reduced pressure thus obtaining a dark oil (10.48 g) which proves to comprise prasterone acetate and intermediate (II) in a 1:3 ratio (areas of HPLC chromatogram recorded at 220 nm).

The crude mixture obtained is then dissolved in tetrahydrofuran (104 ml).

Bis(triphenylphosphine)palladium(II)dichloride Pd(PPh$_3$)$_2$Cl$_2$ (375 mg), diethyl(pyridyl)borane (2.36 g) and an aqueous solution of sodium carbonate (21 ml, 3.5 g of sodium carbonate) are added under agitation at 20-25° C.

The system is refluxed at about 70° C. for 20 hours.

The system is cooled to 20-25° C. and isopropyl acetate (104 ml) and water (104 ml) are added.

The phases are separated and the organic phase is concentrated under reduced pressure after filtration. A dark oil is obtained (10.52 g), which proves to comprise prasterone acetate and abiraterone acetate.

The crude mixture obtained is then dissolved in methanol (32 ml) and the solid, which proves to be unreacted diethyl (pyridyl)borane, is filtered.

The solution is then treated with hydrochloric acid in isopropanol while verifying that the pH remains acid.

It is stirred at 0÷5° C. for 2 hours then the precipitated solid (5.2 g) is filtered, which checked by HPLC analysis against an authentic sample proves to be abiraterone acetate hydrochloride.

The obtained abiraterone acetate hydrochloride is placed under agitation with methylene chloride (50 ml) and an aqueous solution of sodium bicarbonate (50 ml, 3 g), obtaining complete dissolution of the solid. The phases are separated and the dried organic phase is concentrated to dryness at reduced P.

The solid obtained is crystallised from isopropanol obtaining, after drying, 3.8 g of abiraterone acetate (HPLC purity 99.04% recorded at 220 nm), which further checked by means of HPLC-Mass analysis proves to be free from impurity

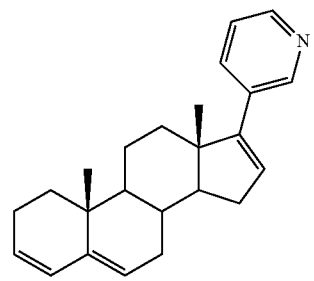 [SMILES: C[C@]12CCC=CC1=CCC1C2CC[C@]2(C)C(c3cccnc3)=CCC12]

The invention claimed is:

1. Process for the preparation of 3β-hydroxyandrost-5,16-dien-17-yl-trifluorornethanesulfonate or 3β-acetoxyandrost-5,16-dien-17-yl-trifluoromethanesulfonate (II) that comprises reacting prasterone or prasterone acetate (III)

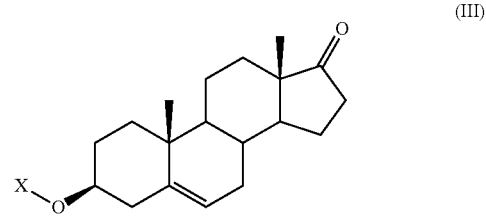

with a bis(trifluoromethanesulfonimide) of formula Ar—N(Tf)$_2$ and a base, to obtain 3β-hydroxyandrost-5,16-dien-17-yl-trifluoromethanesulfonate or 3β-acetoxyandrost-5,16-dien-17-yl-trifluoromethanesulfonate:

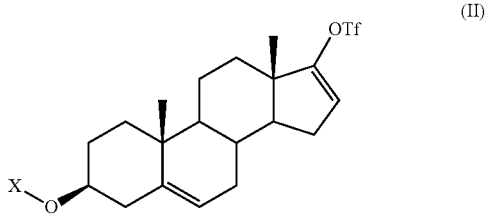

wherein X is hydrogen or the acyl radical CH$_3$—CO—.

2. Process according to claim 1 wherein said bis(trifluoromethanesulfonimide) has formula:

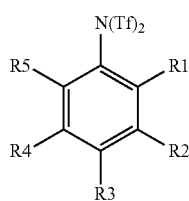

(IV)

wherein:
the aromatic radical is derived from phenyl; and
R1, R2, R3, R4 and R5, independently of each other, can be hydrogen, halogen, —NO$_2$, a linear or branched alkyl radical, an RCONH— amide radical or an RO— alkoxide radical, wherein R is a linear or branched alkyl group.

3. Process according to claim 1 wherein said bis(trifluoromethanesulfonimide) has formula:

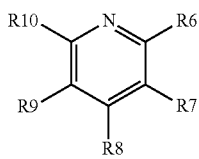

(V)

wherein:
the aromatic radical is derived from pyridine; and
one of R6, R7, R8, R9 and R10 is the —N(Tf)$_2$ radical, while the remaining radicals among R6, R7, R8, R9, and R10, independently of each other, can be hydrogen, halogen, —NO$_2$, a linear or branched alkyl radical, an RCONH— amide radical or an RO— alkoxide radical, wherein R is a linear or branched alkyl group.

4. Process according to claim 2 wherein said bis(trifluoromethanesulfonimide) is N-phenyl-bis(trifluoromethanesulfonimide).

5. Process according to claim 3 wherein said bis(trifluoromethanesulfonimide) is N-(2-pyridyl)-bis(trifluoromethanesulfonimide).

6. Process according to claim 1, wherein said bis(trifluoromethanesulfonimide) is used in an amount between 0.8 and 2 times by weight with respect to the starting prasterone or prasterone acetate.

7. Process according to claim 1, wherein said base is selected from potassium hexamethyldisilazane, lithium hexamethyldisilazane, sodium hexamethyldisilazane, lithium diisopropylamide, lithium tri-sec-butylborohydride, potassium tri-sec-butylborohydride, sodium tert-butoxide and potassium tert-butoxide.

8. Process according to claim 1, wherein the reaction temperature is between −80° C. and 30° C. and the reaction time is between 2 and 24 hours.

9. Process according to claim 1, further comprising the transformation reaction of 3β-hydroxyandrost-5,16-dien-17-yl-trifluoromethanesulfonate or 3β-acetoxyandrost-5,16-dien-17-yl-trifluoromethanesulfonate (II):

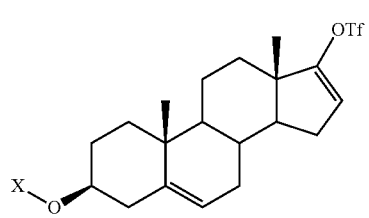

(II)

respectively into abiraterone or abiraterone acetate (I)

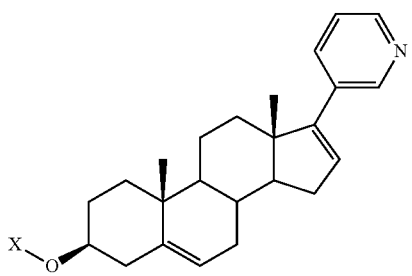

(I)

wherein X is hydrogen or the acyl radical CH$_3$—CO—,
by reacting the mixture resulting from the process of claim 1 with diethyl borane in the presence of a palladium (II) catalyst.

10. Process according to claim 9 wherein said palladium (II) catalyst is bis(triphenylphosphine)palladium(II)dichloride, Pd(PPh$_3$)$_2$Cl$_2$.

* * * * *